United States Patent [19]
Skrabal et al.

[11] Patent Number: 5,372,582
[45] Date of Patent: Dec. 13, 1994

[54] PROBE FOR DIALYSIS

[75] Inventors: Falko Skrabal, Graz; Erich Kleinhappl, Weinitzen, both of Austria

[73] Assignee: AVL Medical Instruments AG, Schaffhausen, Switzerland

[21] Appl. No.: 842,138
[22] PCT Filed: Jul. 30, 1991
[86] PCT No.: PCT/AT91/00092
§ 371 Date: Mar. 23, 1992
§ 102(e) Date: Mar. 23, 1992
[87] PCT Pub. No.: WO92/02270
PCT Pub. Date: Feb. 20, 1992

[30] Foreign Application Priority Data

Jul. 30, 1990 [AT] Austria .................. 1598/90

[51] Int. Cl.⁵ ............ A61M 3/00; A61M 5/178
[52] U.S. Cl. ........................ 604/44; 604/164; 604/169
[58] Field of Search ............. 604/44, 43, 33, 93, 604/158, 164, 169, 4–6

[56] References Cited

U.S. PATENT DOCUMENTS

| | | | |
|---|---|---|---|
| 3,837,339 | 9/1974 | Aisenberg et al. | 128/631 X |
| 4,144,884 | 3/1979 | Tersteegen et al. | 604/158 X |
| 4,180,068 | 12/1979 | Jacobsen et al. | 604/164 X |
| 4,202,332 | 5/1980 | Tersteegen et al. | 604/164 |
| 4,217,895 | 8/1980 | Sagae et al. | |
| 4,265,249 | 5/1981 | Schindler et al. | |
| 4,370,983 | 2/1983 | Lichtenstein | 128/630 |
| 4,464,172 | 8/1984 | Lichtenstein | 128/DIG. 13 X |
| 4,516,580 | 5/1985 | Polyanyi | |
| 4,726,381 | 2/1988 | Jones | 128/632 |
| 4,763,658 | 8/1988 | Jones | 128/635 |
| 4,765,339 | 8/1988 | Jones | 128/632 |
| 4,774,955 | 10/1988 | Jones | 128/632 |

FOREIGN PATENT DOCUMENTS 3342170 6/1984 Germany.

Primary Examiner—Randall L. Green
Assistant Examiner—Elizabeth Burke
Attorney, Agent, or Firm—Watson, Cole, Grindle & Watson

[57] ABSTRACT

A dialytic probe is provided with an insertion needle sharpened at one end, which is surrounded by a flexible plastic cannula, and may be removed after introduction of the probe. The plastic cannula is covered at least partly by a tubular dialyzing membrane which is bonded to the plastic cannula at the distal end and to a handle at the other end, thus forming a fluid-tight seal. The space between the plastic cannula and dialyzing membrane is divided along the length of the probe, such that two passages or lumens of essentially crescent-shaped cross-section are formed, with a flow-connection at the distal end of the plastic cannula, and with a connection to one of separate ingoing and outgoing lines each. The lumen of the plastic cannula may be connected to a drug feeder line. The handle holds the ingoing and outgoing lines and a potential drug feeder line of the probe.

16 Claims, 3 Drawing Sheets

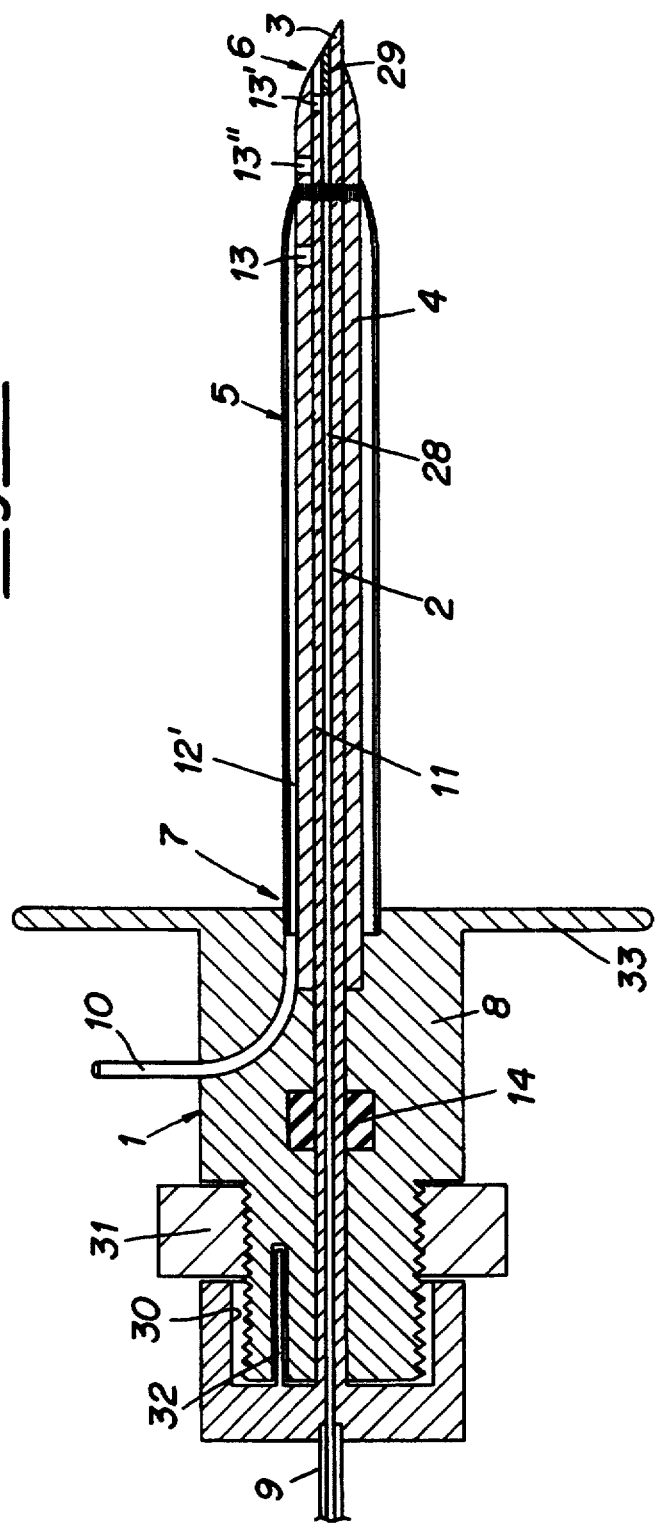

PROBE FOR DIALYSIS

BACKGROUND OF THE INVENTION

The invention relates to a probe for dialysis with an ingoing and an outgoing line for the dialytic medium, comprising an insertion needle for introducing the probe, which needle is surrounded by a flexible plastic cannula, which in turn is surrounded, at least partly, by a tubular dialysing membrane connected to the plastic cannula at the distal end, forming a fluid-tight seal.

In German laid-open print DE-OS 33 42 170 a dialytic probe is disclosed which is used primarily for insertion in biological tissue and comprises a dialysing membrane as well as ingoing and outgoing lines for the dialytic medium. The probe is provided with a frame which supports the dialysing membrane but does not cover it entirely. The frame basically consists of a metal sleeve with an opening in its wall where the surface of the membrane is exposed and may be utilised for dialysis. The size and shape of this opening may vary according to the desired size and shape of the membrane surface available for dialysis, but will always be bounded by parts of the metal sleeve. The dialysing membrane is inserted into the frame with a tight fit against the wall of the frame, the distal ends of membrane and frame being glued together, for instance with the use of epoxide resin. The distal end of the probe is sealed by a semi-circular stopper bounding the interior of the probe. The ingoing and outgoing lines are configured as thin-walled metal tubes passing through a seal at the proximal end of the probe. The opening of one line is next to the distal end, whereas the opening of the other line is inside the probe next to the proximal end of the membrane.

Due to the frame being configured as a metal sleeve, the mechanical strength of the probe is good enough to permit insertion, which may considerably add to the patient's discomfort in certain long-term applications, however. Another disadvantage is that the parts of the probe's surface actually available for dialysis, are comparatively small.

A dialytic probe of the above type is described in U.S. Pat. No. 4,774,955, cf. FIGS. 4 and 5. This probe is provided with a hollow needle, which may be removed after the probe has been introduced, and which is surrounded by a plastic cannula. The plastic cannula in turn is surrounded by a tubular dialysing membrane bonded to the cannula at its distal and proximal end, forming a fluid-tight seal. Through a single feed line a fluid may be introduced into the space between plastic cannula and dialysing membrane, and is drained again through the same line for analysis. For this reason this type of probe will not permit continuous dialysis.

It is an object of the invention to propose a dialytic probe based on the known types of probes described above, which is easy to apply, comfortable to wear for prolonged periods of time, and which guarantees continuous circulation of the dialytic medium.

SUMMARY OF THE INVENTION

In the invention this object is achieved by providing the probe with a handle which has separate ingoing and outgoing lines for feeding and draining the dialytic medium, and by further providing two or more lumens in the probe which are connected to the ingoing and outgoing lines and have a flow connection at the distal end of the plastic cannula, one of which lumens at least is bounded by the dialysing membrane. The distal connecting opening together with the separate ingoing and outgoing lines will ensure a continuous flow of the dialytic medium, the probe itself being easy to apply without causing undue discomfort to the patient.

A simple variant of the invention provides that the lumen of the plastic cannula opening up after the insertion needle is removed, is connected to one of the ingoing and outgoing lines, and that the lumen between plastic cannula and dialysing membrane be connected to the other one of the ingoing and outgoing lines, and further that the distal end of the plastic cannula have a lateral wall opening into the lumen between plastic cannula and dialysing membrane. This will give a dialytic probe in which the parts remaining in the patient's body are made of soft, flexible material, and where the entire surface of the probe may be utilised for the purpose of dialysis.

In applications in which the insertion needle need not be removed from the probe, the proposal is put forward that the lumen between plastic cannula and dialysing membrane be connected to one of the ingoing and outgoing lines, and that the insertion needle be configured as a hollow needle up to a lateral wall opening at the distal end, the other one of the ingoing and outgoing lines being integrated into the needle handle, and the insertion needle being retractable after the introduction of the probe, up to the point where its lateral wall opening coincides with a distal wall opening in the plastic cannula.

Such a probe may be additionally used for applying a drug, if the wall of the plastic cannula is provided with another lateral opening in a distal region not covered by a membrane, which opening will coincide with the opening in the wall of the insertion needle after the latter has been moved axially.

The invention also provides means for the axial positioning of the insertion needle as well as elements for keeping the insertion needle from turning.

In another variant of the invention the space between plastic cannula and dialysing membrane is divided along the length of the dialytic probe, forming two lumens of essentially crescent-shaped cross-section, with a flow-connection at the distal end of the plastic cannula and with a connection to one of the separate ingoing and outgoing lines each, and the lumen of the plastic cannula opening up after removal of the insertion needle may be connected to a drug feeder line in the handle. It is an additional advantage of this variant that the inner lumen of the plastic cannula may be used for delivering a drug independently of the remaining dialytic system, after the insertion needle has been removed; this is not possible with the system described in the above DE-OS 33 42 170, for example.

According to the invention the latter variant is obtained by bonding the dialysing membrane to the plastic cannula by glueing or welding, two of the beads or welds running essentially along the length of the dialytic probe, and an annular bead or weld being placed at the distal end, the longitudinal beads or welds being separated from the annular bead or weld by at least one gap establishing the flow connection between the two lumens, or by attaching the dialysing membrane to two webs running essentially along the length of the dialytic probe, and, possibly, to a distal, annular web of the plastic cannula, the longitudinal webs being separated from the annular one by at least one gap establishing the flow connection between the two lumens. The distal web should be configured such that it connects to the core of the probe without forming a step.

Suitable materials for the plastic cannula are polyolefins (polypropylene, polyethylene), which are oxidised and bonded to the dialysing membrane by means of epoxide resins or polycyanates.

If the materials used for the plastic cannula and the dialysing membrane are not suited for bonding and welding, the invention may provide that the dialysing membrane be mechanically fastened to the longitudinal webs and, possibly, the annular web, i.e., preferably by clamping. This may be achieved by providing a groove or notching the webs.

Another preferable variant of the invention proposes that the plastic cannula have a lumen which opens up after the insertion needle is removed, and which is connected to a drug feeder line, and that a further lumen be provided in the wall of the plastic cannula, which is connected to one of the ingoing and outgoing lines, and that the lumen between plastic cannula and dialysing membrane be connected to the other one of the ingoing and outgoing lines, the lumen in the wall of the plastic cannula having at least one wall opening into the lumen bounded by the dialysing membrane. This variant again provides a closed system of dialysis with the additional possibility of drug delivery.

An enhanced variant of the invention provides that the handle of the dialytic probe contain the plastic cannula in a center bore, the handle being tapered towards the distal end of the plastic cannula, such that the dialysing membrane may be slipped over the exterior face of the handle and attached thereto.

According to a proposal put forward by the invention the dialysing membrane is slipped over the handle more easily if its end facing the handle has a larger diameter than at the distal end of the plastic cannula.

Manufacture is facilitated by providing channels in the centre bore of the handle, which channels, together with the inserted plastic cannula, form flow connections between at least one of the ingoing and outgoing lines and at least one lumen between plastic cannula and dialysing membrane. The flow connections inside the handle may be moulded into the component during manufacture, for instance, by injection moulding.

It may be advantage if the dialysing membrane is not taut but folded in the area where it is attached to the handle, in order to prevent its edges from tearing as the plastic cannula bends. The dialytic probe is introduced up to the part of the handle covered by the membrane, in order to prevent the entrance of air or leakage of the dialytic medium.

Although the dialytic probe may be plugged manually after the insertion needle has be removed, for instance, by means of a stopper, the proposal is put forward in another variant of the invention that the handle of the probe be furnished with a flexible stopper pierced by the insertion needle, which stopper plugs the probe automatically in the area of the handle after removal of the insertion needle.

Finally, the invention provides that the dialysing membrane be made of resilient material permitting elastic deformation if subject to the pressure of the dialytic medium. Thus the active surface of the membrane may be enlarged even after the probe has been introduced. By varying the pressure of the dialytic medium the size of the pores of the dialysing membrane may be adjusted.

A membrane of cellophane, for example, may be fitted over the plastic cannula, which membrane will swell by up to 20 per cent only upon contact with the dialytic medium, thus providing the space for the dialytic flow.

As the plastic cannula and the dialysing membrane may be made of related or compatible materials (the invention specifies cellophane, cuprophane, polyurethane, polycarbonate or polyurethane with incorporated polyether, etc.), these materials can easily be bonded or welded together.

Following is a more detailed description of the invention as illustrated by the attached drawings.

BRIEF DESCRIPTION OF THE DRAWINGS

FIG. 12 shows a variant according to FIG. 1.

DETAILED DESCRIPTION OF THE PREFERRED EMBODIMENTS

Figure 1:
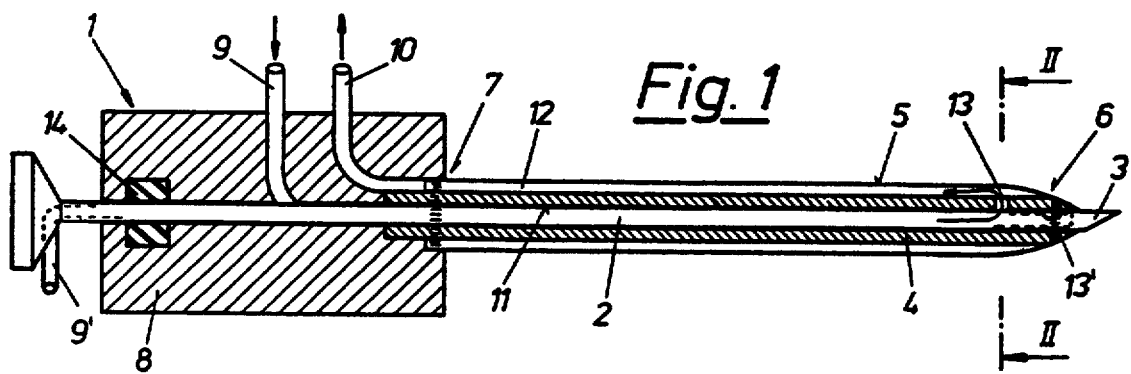
FIG. 1 is a schematic view of a dialytic probe as described by the invention.
Figure 2:
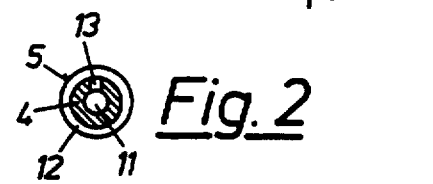
FIG. 2 is a section of the distal end of the probe as seen along line II—II in FIG. 1, FIGS. 3, 5, 7 show variants of the probe of the invention.

The embodiment of a dialytic probe 1 presented in FIGS. 1 and 2 has an insertion needle 2, which is surrounded by a flexible plastic cannula 4 that leaves the sharpened or pointed end 3 of the needle exposed. The plastic cannula, 4 is covered by a tubular dialysing membrane 5, which is attached to the plastic cannula at the distal end 6 and to a handle 8 of the probe 1 at the other end 7, forming a fluid-tight seal. The bond may be achieved by glueing or welding. The handle 8 is provided with ingoing and outgoing lines 9, 10 for the dialytic medium, the ingoing line 9 leading into the lumen 11 of the plastic cannula 4 opening up after removal of the insertion needle 2, and the outgoing line 10 being connected with the lumen 12 between plastic cannula 4 and tubular dialysing membrane 5. At the distal end 6 of the plastic cannula 4 is located a lateral wall opening 13, which leads into the exterior lumen 12 and establishes a flow connection for the dialytic medium. Any leakage of the dialytic fluid at the distal end of the probe will be prevented by the tissue surrounding the probe. The handle 8 of the probe is furnished with a flexible stopper 14 pierced by the insertion needle 2, which will automatically plug the probe 1, or rather, the interior lumen 11 of the plastic cannula 4 upon removal of the insertion needle 2. In the context of FIG. 1 a variant would be possible in which the insertion needle 2 is hollow up to a distal lateral opening 13', with an ingoing or outgoing line 9' in the handle. After introduction of the probe the insertion needle 2 is retracted until openings 13 and 13' coincide, thus providing a closed system of circulation for the dialytic medium. In this instance line 9 in the handle 8 is superfluous, of course.

For accurate axial positioning of the insertion needle the latter may be provided with an annular groove next to the handle (not shown here in detail) engaging knobs or similar projections that are located in or on the handle. The insertion needle 2 may be advanced until the wall opening 13' is no longer covered by the plastic cannula 4. In this position a drug may be delivered via line 9'. A variant in which the insertion needle 2 remains in the probe, is presented in FIG. 12 to be discussed in more detail below.

Figure 3:
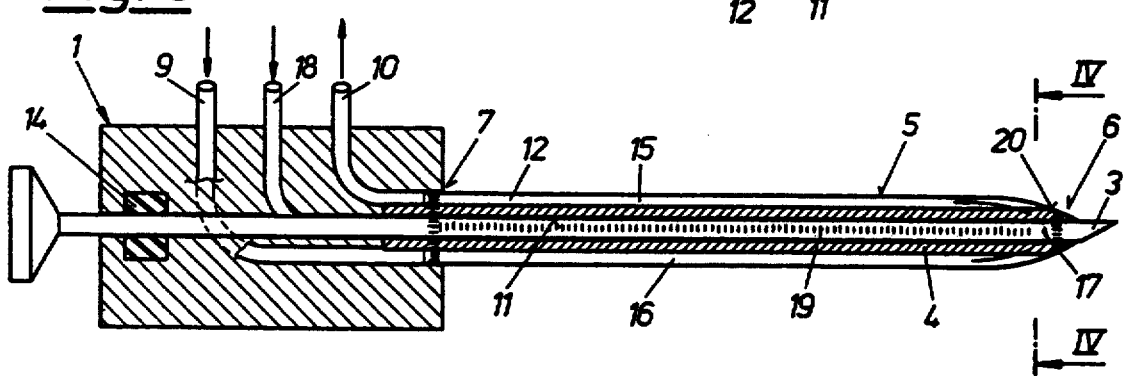
Figures 4, 5:
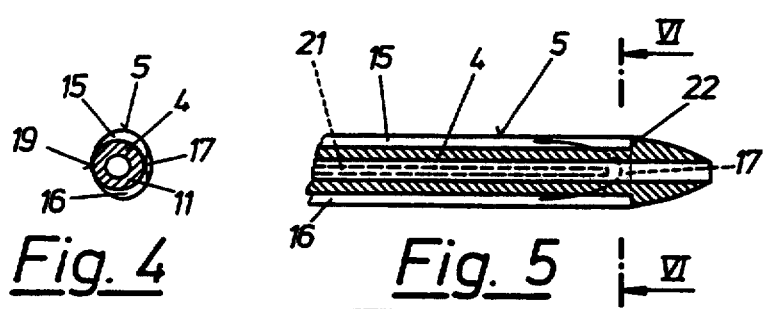
FIGS. 4, 6, 8 are sections of variants of the invention in a plane corresponding to that of FIG. 2.
Figure 6:
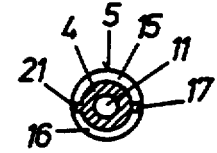

The variant of FIGS. 3 and 4 shows a dialytic probe with a completely closed system of circulation for the dialytic medium. The lumen 12 between plastic cannula 4 and dialysing membrane 5 is divided along the length of the probe by two bonds or welds, resulting in two lumens 15, 16 of essentially crescent-shaped cross-section, as shown in FIGS. 4 and 6. The two lumens 15, 16 have a flow connection 17 at the distal end 6, effecting a flow reversal of the dialytic medium within the probe, as indicated by an arrow. For example, lumen 16 is connected to the ingoing line 9, and lumen 15 to the outgoing line 10. The interior lumen 11 of the plastic cannula 4 is not required for carrying the dialytic medium and is connected to a drug feeder line 18, which is also situated in the handle 8.

As shown in FIGS. 3 and 4, the dialysing membrane 5 may be attached to the plastic cannula 4 by way of two bonds or welds 19 along the length of the probe 1, and by a distal, annular bond or weld 20 (or by mechanical fastenings). At least one of the longitudinal bonds or welds 19 is separated from the annular bond or weld 20 by a gap providing the flow connection 17 between the two lumens 15 and 16.

The variant of FIGS. 5 and 6 differs from that of FIGS. 3 and 4 only in that the division of the exterior lumen into the two lumens 15 and 16 is effected by webs 21 along the length of the probe essentially. A radial web 22 may be provided, in which instance at least one of webs 21 is not connected to the radial web 22, leaving a gap for the flow connection 17 between the two lumens 15 and 16. The division along the length of the probe by webs 21 or bonds or welds 19 need not be a straight line but may be helical to increase the length of the dialytic path.

Figure 7:
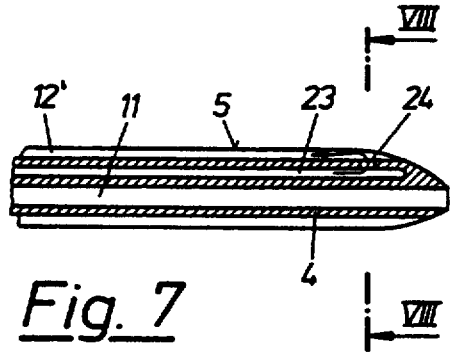
Figure 8:
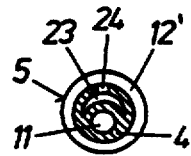

The variant of FIGS. 7 and 8 also shows a closed dialytic circuit, in which the plastic cannula 4 has a lumen 23 in its wall, in addition to lumen 11. Lumen 23 is connected to the feeder line for the dialytic medium (not shown here), for instance, a wall opening 24 being provided in this case, which leads into the exterior lumen 12' bounded by the tubular dialysing membrane 5.

Figure 9:
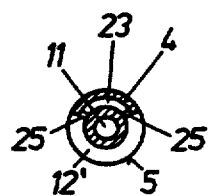
FIG. 9 shows a further variant of the invention, the plane corresponding to that of FIG. 2.

In the variant shown in FIG. 9 the dialysing membrane 5 surrounds the plastic cannula 4 only partially. In this case the dialytic medium is delivered through the lumen 23 in the wall of the cannula 4 and is drained through the exterior lumen 12'. The flow connection in the distal region is effected by openings 25. Lumen 11 again is available as a drug feeder line.

Figure 10:
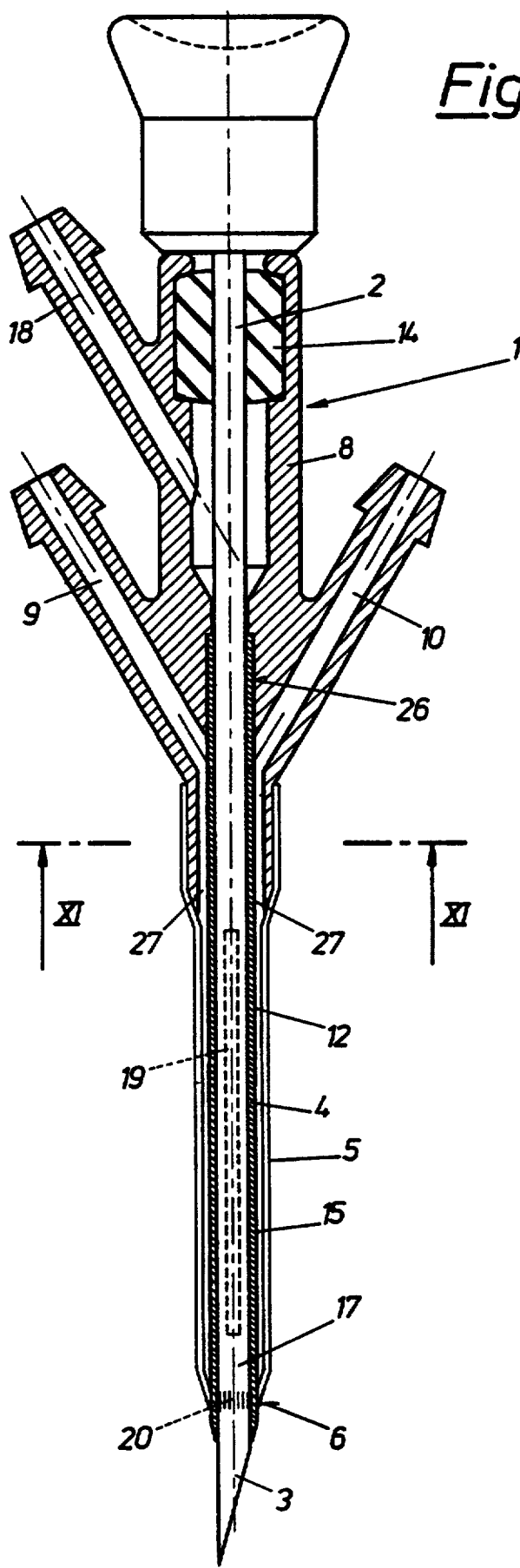
FIG. 10 shows a variant according to FIG. 3.
Figure 11:
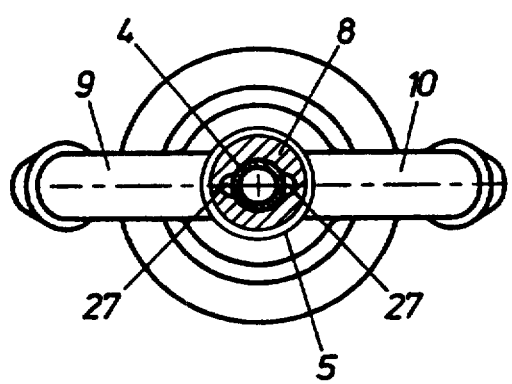
FIG. 11 is a section along line XI—XI in FIG. 10.

The variant presented in FIGS. 10 and 11 is particularly well suited for series production. The handle 8 of the probe is an injection moulded part, for example, in which the plastic cannula 4 is held in a centre bore 26. The handle 8 is tapered towards the distal end 6 of the plastic cannula 4, such that the dialysing membrane 5 may be slipped over the exterior face of the handle, where it may be attached by bonding, welding or clamping. To facilitate the slipping-on of the membrane, the diameter of the dialysing membrane 5 is enlarged in the area of the handle 8. The centre bore 26 has lateral channels 27, which, together with the plastic cannula 4 inserted into the bore 26, form flow connections linking the ingoing line 9 and lumen 16 on the one hand, and lumen 15 and the outgoing line 10 on the other hand. The dialytic probe in FIG. 10 is introduced up to the part of the handle 8 covered by the dialysing membrane 5.

The variant of FIG. 12 shows a dialytic probe 1, in which the insertion needle 2 is configured as a hollow needle up to a distal, lateral wall opening 13'. At the handle the ingoing line 9 enters the hollow needle, at the other end the lumen 28 of the needle is blocked by a plug 29. Again, the insertion needle 2 is retracted after introduction of the probe to a point where its lateral wall opening 13' coincides with the distal wall opening 13 of the plastic cannula 4, to establish the dialytic circuit. In a distal area not covered by the membrane the plastic cannula 4 has a further opening 13" in the side of its wall, which may be made to coincide with the wall opening 13' of the insertion needle 2 after the latter has been moved axially. In this position a drug may be applied.

Axial positioning of the insertion needle 2 may be effected by means of a thread 30 on the handle 8 cooperating with a setting nut 31 acting on the needle handle. The setting nut 31 and the handle 8 may have markings indicating the axial position of the insertion needle 2. Other known positioning means may also be used.

To protect the insertion needle 2 from turning within the plastic cannula 4, a locking element 32 is provided. By means of a disk 33 the probe may be fastened securely to the patient's body.

Finally, this variant would also permit the removal of the insertion needle 2 after the probe has been introduced, and its replacement by a comparatively soft mandrel with a lumen 28 taking over the functions of the hollow needle.

All main parts of the plastic cannula 4 of the individual variants, including lumen 23 and the longitudinal webs 21, are machine-made, e.g., extrusion-moulded, and require only a minimum of tooling, e.g., drilling openings 13, 24, 25, fitting the dialysing membrane 5, and fastening the handle 8.

We claim:
1. A probe for dialysis comprising:
   a handle,
   a flexible plastic cannula which has a proximal end and a distal end, said proximal end being sealingly connected to said handle,
   a tubular dialysing membrane positioned around at least a portion of said flexible plastic cannula and defining a proximal end and a distal end, said proximal end of said membrane being sealingly connected to said handle and said distal end of said membrane being sealingly connected to said cannula, said cannula forming at least a wall of first and second lumens of said probe which are in fluid communication with one another at said distal end of said cannula, said membrane forming a wall portion of at least said first lumen, and
   an axially movable needle which extends through said handle and said cannula to a tip end which is positionable beyond said distal end of said cannula, said handle defining a first fluid medium channel in fluid communication with said first lumen.

2. A probe for dialysis according to claim 1, wherein said handle defines a second fluid medium channel, wherein said second lumen opens up in said plastic cannula after said insertion needle is removed from within said handle and is in fluid communication with said second fluid medium channel, wherein said first lumen is situated between said plastic cannula and said dialysing membrane, and wherein said distal end of said plastic cannula has a lateral wall opening into said second lumen.

3. A probe for dialysis according to claim 1, wherein said first lumen is situated between said plastic cannula and said dialysing membrane, wherein said insertion needle is configured as a hollow needle up to a lateral wall opening at a distal end of said hollow needle, wherein said insertion needle includes a needle handle that defines a second fluid medium channel, and wherein said insertion needle is retractable up to a point where said lateral wall opening coincides with a distal wall opening in said plastic cannula.

4. A probe for dialysis according to claim 3, wherein said plastic cannula is provided with a second lateral wall opening in a distal region not covered by said dialysing membrane, said second lateral opening coinciding with said wall opening of said insertion needle after axial movement of said needle.

5. A probe for dialysis according to claim 3, including means to axially move said insertion needle and elements for preventing said insertion needle from turning.

6. A probe for dialysis according to claim 1, wherein a space between said plastic cannula and said dialysing membrane is divided along a length of said probe to form said first and second lumens of essentially crescent-shaped cross-section and having a flow-connection at said distal end of said plastic cannula, wherein said handle defines a second fluid medium channel which is in fluid communication with said second lumen, and wherein a third lumen opens up in said plastic cannula after removal of said insertion needle from within said handle, said third lumen being connected to a drug feeder line defined in said handle.

7. A probe for dialysis according to claim 6, wherein said dialysing membrane is bonded to said plastic cannula by gluing or welding and two longitudinal beads or welds extending essentially along said length of said probe, and an annular bead or weld is placed at said distal end of said plastic cannula, said longitudinal beads or welds being separated from said annular bead or weld by at least one gap that provides a flow connection between said first and second lumens.

8. A probe for dialysis according to claim 6, wherein said dialysing membrane is attached to two longitudinal webs running essentially along said length of said probe, and to a distal, annular web of said plastic cannula, said longitudinal webs being separated from said annular web by at least one gap that provides a flow connection between said first and second lumens.

9. A probe for dialysis according to claim 8, including a clamp for mechanically fastening said dialysing membrane to said longitudinal and annular webs.

10. A probe for dialysis according to claim 1, wherein said second lumen opens up in said plastic cannula after said insertion needle is removed and is connected to a drug feeder line, wherein a third lumen is provided in a wall of said plastic cannula, said third lumen being connected to a second fluid medium channel, and wherein said first lumen is situated between said plastic cannula and said dialysing membrane, said third lumen in said wall of said plastic cannula having at least one wall opening into said first lumen bounded by said dialysing membrane.

11. A probe for dialysis according to claim 1, wherein said handle of said probe contains said plastic cannula in a center bore, and is tapered towards said distal end of said plastic cannula, such that said dialysing membrane may be slipped over an exterior face of said handle and attached thereto.

12. A probe for dialysis according to claim 11, wherein channels are provided in said centre bore of said handle, said channels, together with said inserted plastic cannula, forming a flow connection between at least one of said ingoing and outgoing lines and at least one of said lumens between said plastic cannula and said dialysing membrane.

13. A probe for dialysis according to claim 11, wherein one end of said dialysing membrane facing said handle has a larger diameter than at said distal end of said plastic cannula.

14. A probe for dialysis according to claim 1, wherein said handle of said probe includes a flexible stopper pierced by said insertion needle, said stopper plugging said probe automatically after removal of said insertion needle from within said handle.

15. A probe for dialysis according to claim 1, wherein said dialysing membrane is made of resilient material permitting elastic deformation if subjected to pressure of a dialytic medium.

16. A probe for dialysis according to claim 1, wherein said dialysing membrane is made of a material from the group consisting of cellophane, cuprophane, polycarbonate, polyurethane and polyurethane with incorporated polyether.

* * * * *